United States Patent
Arai et al.

[11] Patent Number: 4,845,259
[45] Date of Patent: Jul. 4, 1989

[54] NOVEL ORGANOSILANE COMPOUNDS

[75] Inventors: Masatoshi Arai; Tsuneo Kimura, both of Annaka, Japan

[73] Assignee: Shin-Etsu Chemical Co., Ltd., Japan

[21] Appl. No.: 144,465

[22] Filed: Jan. 19, 1988

[30] Foreign Application Priority Data

Jan. 19, 1987 [JP] Japan .................. 62-9661

[51] Int. Cl.$^4$ .............................................. C07F 7/08
[52] U.S. Cl. .............................................. 556/440
[58] Field of Search ................................. 556/440

[56] References Cited

U.S. PATENT DOCUMENTS

| | | | |
|---|---|---|---|
| 3,317,369 | 5/1967 | Clark et al. | 556/440 X |
| 3,377,371 | 4/1968 | Quaal | 556/440 |
| 3,427,337 | 2/1969 | Miller et al. | 556/440 |
| 3,746,734 | 7/1973 | Berger et al. | 556/440 |
| 4,575,595 | 3/1986 | Nakos et al. | 556/440 X |

*Primary Examiner*—Paul F. Shaver
*Attorney, Agent, or Firm*—Lowe, Price, LeBlanc, Becker & Shur

[57] ABSTRACT

Novel organosilane compounds of the following general formula

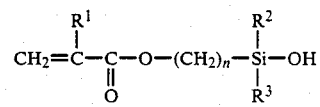

in which $R^1$ is a hydrogen atom or a methyl group, $R^2$ and $R^3$ are independently an unsubstituted or substituted monovalent hydrocarbon group, and n is an integer of 1, 2 or 3. The compounds are reactive with other reactive group-bearing copounds and are effective for potting, sealing or coating of electric and electronic parts.

13 Claims, 2 Drawing Sheets

NOVEL ORGANOSILANE COMPOUNDS

BACKGROUND OF THE INVENTION

Field of the Invention

This invention relates to hitherto unknown, novel organosilicon compounds having an acrylic or methacrylic moiety and a hydroxyl group directly bonded or joined to the silicon atom. These compounds are reactive and are very useful for potting, sealing and/or coating of, for example, electric and electronic parts.

SUMMARY OF THE INVENTION

It is an object of the invention to provide new and hitherto unknown organosilane compounds which have wide utility especially in the field of electric and electronic industries.

It is another object of the invention to provide novel organosilane compounds which have an acrylate or methacrylate group, so that they are polymerizable by application of heat or light.

It is a further object of the invention to provide novel organosilane compounds having a reactive hydroxyl group as well as the unsaturated ester group mentioned above, and can readily convert into unsaturated group-bearing derivatives by reaction of the hydroxyl group with other compounds having a group reactive with the hydroxyl group.

It is a still further object of the invention to provide novel, very reactive organosilane compounds which are convertible into photo-reactive or photocurable materials by reaction with low molecular weight silanes and siloxanes, or high molecular weight siloxanes.

These objects can be achieved, according to the invention, by an organosilane compound of the following general formula (I)

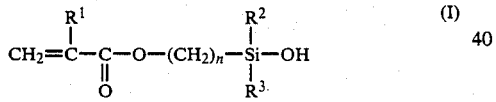

in which $R^1$ represents a hydrogen atom or a methyl group, $R^2$ and $R^3$ independently represent a monovalent hydrocarbon group selected from an alkyl group having from 1 to 6 carbon atoms, a cycloalkyl group, an alkenyl group having from 2 to 6 carbon atoms and an aryl group with or without being substituted partly or wholly, and n is an integer of from 1 to 3. Specific and preferable examples of the organosilane compound are those compounds of the formula in which both $R^2$ and $R^3$ are a methyl group or one or both of $R^2$ and $R^3$ are a phenyl group provided that if one of $R^2$ and $R^3$ is a phenyl group, the other is a methyl group, $R^1$ is a hydrogen atom or a methyl group, and n is 1 or 3. Most preferably, $R^2$ and $R^3$ are independently a methyl group.

DETAILED DESCRIPTION AND EMBODIMENTS OF THE INVENTION

Figure 1:
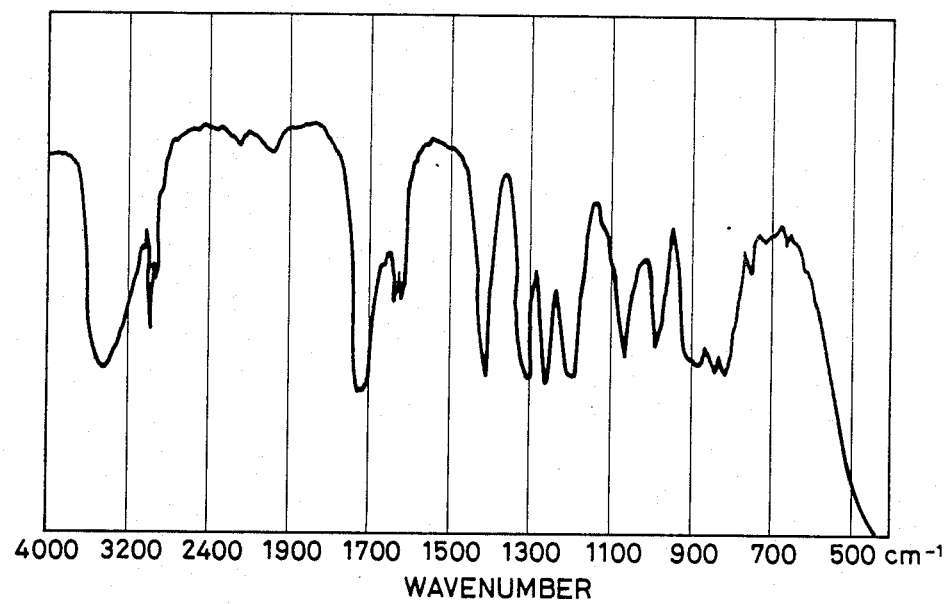
FIGS. 1 to 4 are infrared absorption spectrum charts of organosilanes obtained in Examples 1 to 4, respectively.

The organosilane compounds according to the invention are represented by the formula (I) indicated before.

In the formula, $R^1$ is a hydrogen atom or a methyl group and $R^2$ and $R^3$ independently represent an unsubstituted or substituted monovalent hydrocarbon group, and n is an integer of from 1 to 3. The unsubstituted monovalent hydrocarbon group may include an alkyl group having from 1 to 6 carbon atoms such as a methyl group, an ethyl group, a propyl group, a butyl group and the like; a cycloalkyl group such as a cyclohexyl group; an alkenyl group having from 2 to 6 carbon atoms such as a vinyl group, an allyl group and the like; and an aryl group such as a phenyl group, a tolyl group and the like. The part or all of the hydrogen atoms joined or bonded to the carbon atom or atoms of the above hydrocarbon groups may be substituted with a halogen atom, a cyano group, and the like. Specific examples of the substituted group include a chloromethyl group, a trifluoropropyl group, a cyanoethyl group, and the like. Of these groups, the methyl group or phenyl group for both or either of $R^2$ and $R^3$ is preferred because of the availability of starting silanes having such groups. Most preferably, both $R^2$ and $R^3$ are a methyl group.

Specific and preferable examples of the organosilane compounds of the invention are those of the following formulae (a) to (l)

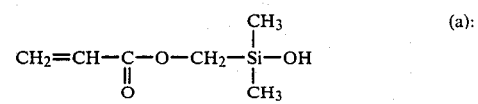

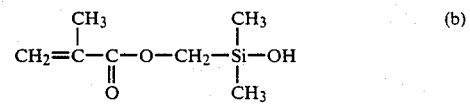

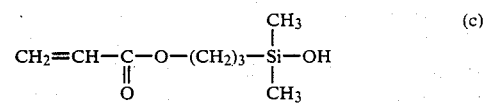

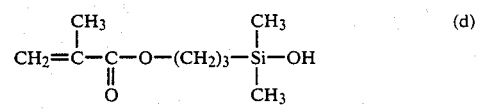

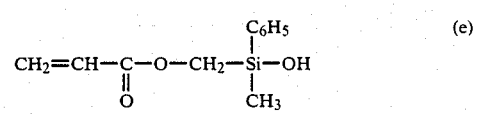

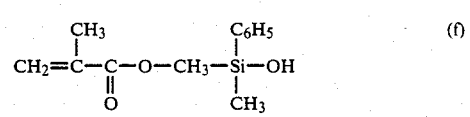

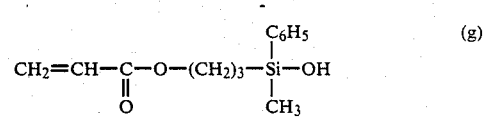

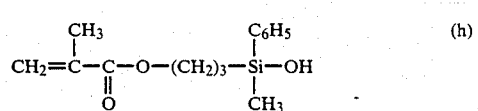

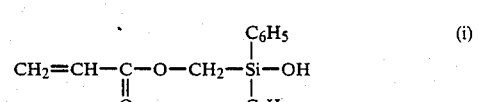

-continued

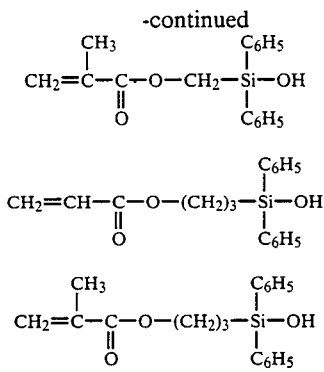

As will be apparent from the foregoing general and specific formulae, the organosilane of the present invention has an acrylate or methacrylate group bonded to the silicon atom through the carbon atom and a hydroxyl group directly bonded to the silicon atom.

These compounds are prepared according to the following reaction sequence:

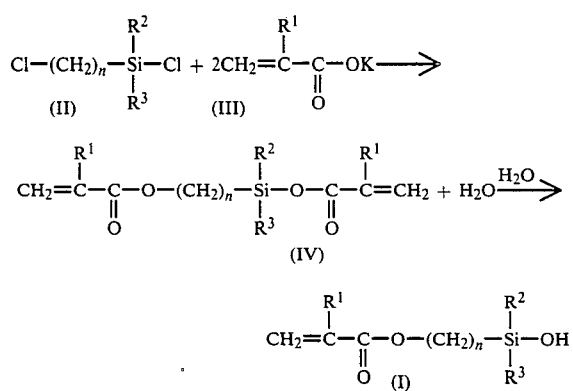

In the above reaction sequence, a chloroalkylsilane of the general formula (II) is reacted with a metal salt of an alpha,beta-unsaturated carboxylic acid of the formula (III) to obtain a di(meth)acrylate of the formula (IV). The di(meth)acrylate is hydrolyzed to obtain a compound of the formula (I). In these formulae, $R^1$, $R^2$, $R^3$ and n have, respectively, the same meanings as defined with respect to the formula (I). The metal salts of the unsaturated carboxylic acids may be alkali metal acrylates or methacrylates such as potassium acrylate, potassium methacrylate, sodium acrylate, sodium methacrylate and the like. The reaction between the starting compounds of the formulae (II) and (III) is usually effected in a solvent under heating conditions of 80° to 120° C. for 2 to 5 hours. The resultant reaction solution is dropped or poured into an aqueous solution of a weakly alkaline substance for hydrolysis at 20° to 50° C. The hydrolyzate may be collected by any ordinary techniques such as solvent extraction. The solvent for the reaction may be an amine compound such as dimethylformamide, hexamethylphosphoamide and the like. The reaction is carried out in the presence of a tertiary amine hydrochloride such as trimethylamine hydrochloride, triethylamine hydrochloride or the like.

The organosilane compounds of the formula (I) according to the invention are novel and hitherto unknown compounds. Since these compounds have reactive functional groups therein including an acrylate or methacrylate group bonded to the silicon atom through the carbon atom and the hydroxyl group directly bonded to the silicon atom, these compounds are considered to be utilized in various fields. The unsaturated ester group will have a thermal or photopolymerizable function and the hydroxyl group will readily react with a chlorine substituent or an alkoxy group of compounds. The reactivity of the hydroxyl group is very advantageous in simply yielding various derivatives having the unsaturated ester group by reaction of the compound of the invention with a reactive group-bearing compound. For instance, when the compound of the invention is reacted with low molecular weight silanes or siloxanes, photopolymerizable oligomers, diluents, adhesives and the like may be obtained. Further, when the compound of the invention is introduced into high molecular weight siloxanes, photopolymerizable rubbers, varnishes, gels and the like may be obtained. These modified products can be conveniently used for potting, sealing and coating of electric and electronic parts. This is a great merit from the industrial viewpoint.

The present invention is more particularly described by way of examples.

EXAMPLE 1

69 g (0.63 moles) of potassium acrylate, 100 g of toluene, 9 g of dimethylformamide, and 0.1 g of 2,6-t-butyl-4-methylphenol were charged into a reactor and subjected to azeotropic dehydration. Thereafter, 36 g (0.25 moles) of chloromethyldimethylchlorosilane was dropped into the reaction mixture in about 15 minutes. After completion of the dropping, the mixture was heated and reacted at 110° C. for 3 hours. The reaction solution was dropped into an aqueous sodium hydrogencarbonate solution, after which the formed salt was removed, followed by extraction with toluene. The resultant organic phase was collected and subjected to distillation under reduced pressure to obtain 28 g of a liquid having a boiling point of 80° C./4 mmHg.

The thus obtained liquid was subjected to elementary analysis and IR analysis and also to gas mass spectroscopy to determine the molecular weight along with a refractive index and a specific gravity. From these analyses, the compound obtained was confirmed to have the following formula

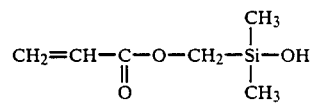

The results of the analyses are shown below.

| Elementary analysis: | C | H | Si |
|---|---|---|---|
| Calculated for $C_6H_{12}O_3Si$ (%) | 44.97 | 7.55 | 17.53 |
| Found (%) | 44.99 | 7.53 | 17.51 |

Molecular weight: 160.
Refractive index: 1.4423.
Specific gravity: 1.0198.
IR absorption spectrum: see FIG. 1.

EXAMPLE 2

The general procedure of Example 1 was repeated except that 78 g (0.63 g) of potassium methacrylate was used instead of the potassium acrylate, thereby obtaining 30 g of a liquid having a boiling point of 60° C./2 mmHg. This liquid was analyzed similarly to Example 1 with the following results, from which the compound obtained was confirmed to have the following formula

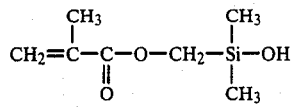

| Elementary analysis: | C | H | Si |
|---|---|---|---|
| Calculated for $C_7H_{14}O_3Si$ | 48.24 | 8.10 | 16.07 |
| Found | 48.23 | 8.08 | 16.09 |

Figure 2:
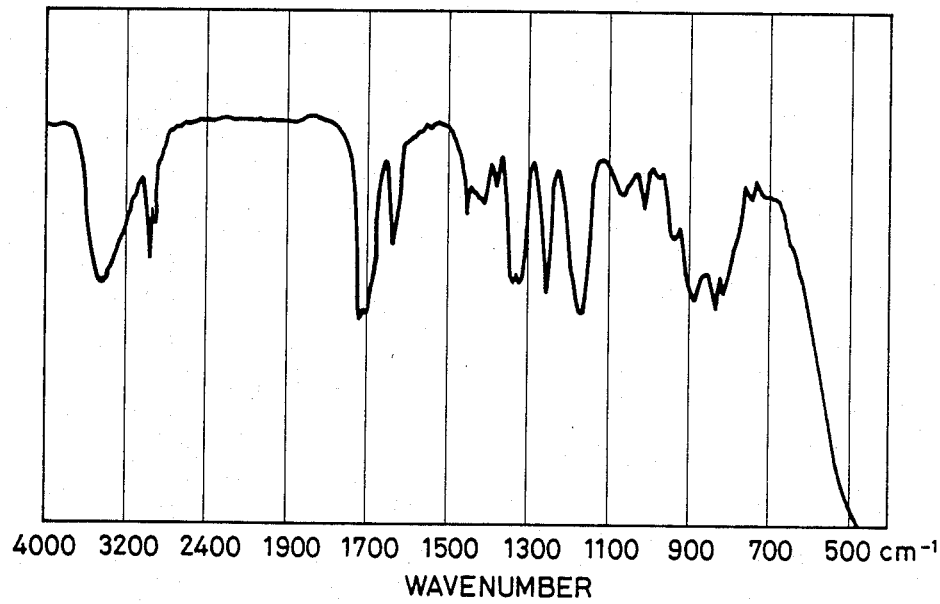

Molecular weight: 174.
Refractive index: 1.4442.
Specific gravity: 1.0050.
IR absorption spectrum: see FIG. 2.

EXAMPLE 3

28 g (0.25 moles) of potassium acrylate, 70 g of dimethylformamide, 30 g of toluene, 0.1 g of 2,6-di-t-butyl-4-methylphenol and 0.1 g of trimethylamine hydrochloride were charged into a reactor and subjected to azeotropic dehydration, into which 17 g (0.1 mole) of chloropropyldimethylchlorosilane was dropped in about 5 minutes. After completion of the reaction, the mixture was thermally reacted at 120° C. for 6 hours. The resultant reaction solution was dropped into an aqueous sodium hydrogencarbonate solution, followed by removal of the formed salt, extraction with toluene. The extract was washed with water and distilled under reduced pressure to obtain 10 g of a liquid having a boiling point of 100° C./2 mmHg.

This liquid was subjected to elementary, IR and gas mass spectrum analyses and measurement of a refractive index and a specific gravity with the following results, from which the liquid was confirmed to be a compound of the following formula

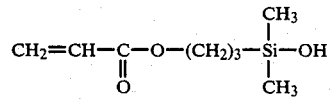

| Elementary analysis: | C | H | Si |
|---|---|---|---|
| Calculated for $C_8H_{16}O_3Si$ (%) | 51.03 | 8.57 | 14.92 |
| Found | 51.01 | 8.58 | 14.95 |

Figure 3:
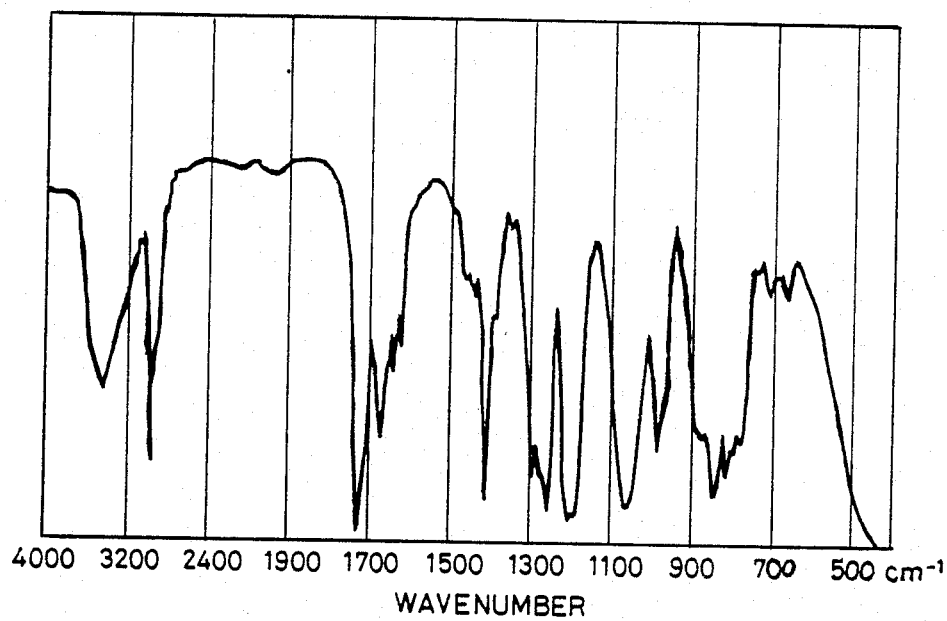

Molecular weight: 188.
Refractive index: 1.4467.
Specific gravity: 0.9854.
IR absorption spectrum: see FIG. 3.

EXAMPLE 4

The general procedure of Example 3 was repeated except that 31 g (0.25 moles) of potassium methacrylate was used instead of the potassium acrylate, thereby obtaining 16 g of a liquid having a boiling point of 110° C./2 mmHg. This liquid was subjected to the analyses in the same manner as in Example 3, from which it was confirmed that the liquid was a compound of the following formula

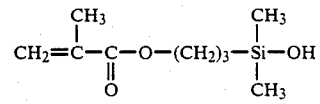

The results of the analyses are shown below.

| Elementary analysis: | C | H | Si |
|---|---|---|---|
| Calculated for $C_9H_{18}O_3Si$ | 53.43 | 8.97 | 13.88 |
| Found | 53.42 | 8.95 | 13.90 |

Figure 4:
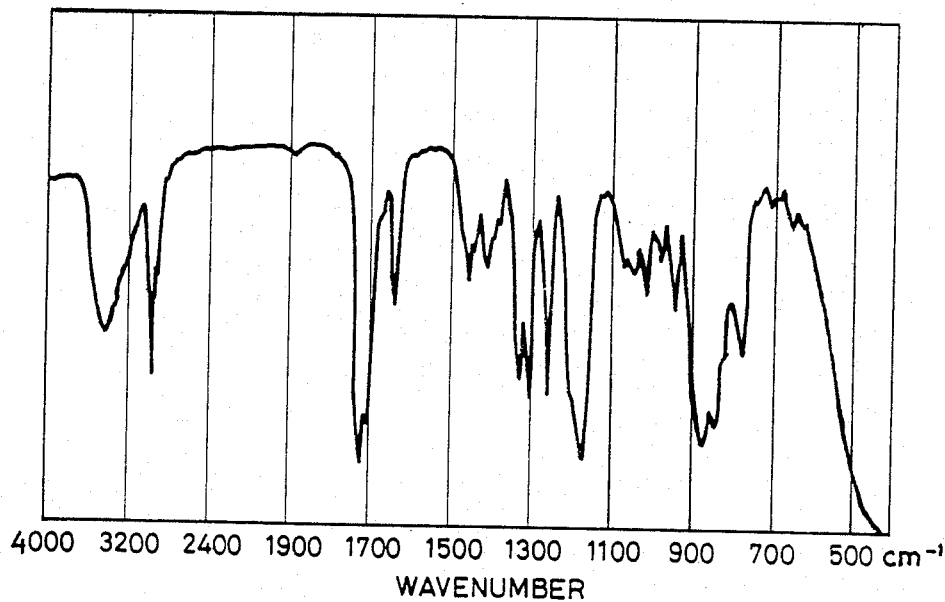

Molecular weight: 202.
Refractive index: 1.4511.
Specific gravity: 0.9860.
IR absorption spectrum: see FIG. 4.

What is claimed is:

1. An organosilane compound of the following general formula (I)

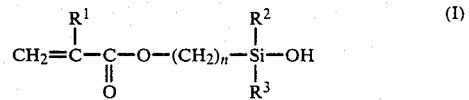

in which $R^1$ represents a hydrogen atom or a methyl group, $R^2$ and $R^3$ independently represent a monovalent hydrocarbon group selected from the group consisting of an alkyl group having from 1 to 6 carbon atoms, a cycloalkyl group, an alkenyl group having from 2 to 6 carbon atoms and an aryl group which may have at least one substituent, and n is an integer of from 1 to 3.

2. An organosilane compound according to claim 1, wherein said monovalent hydrocarbon group is an alkyl group.

3. An organosilane compound according to claim 2, wherein said alkyl group is a methyl group.

4. An organosilane compound according to claim 1, wherein $R^2$ and $R^3$ are both a methyl group.

5. An organosilane compound according to claim 1, wherein said monovalent hydrocarbon group is a phenyl group.

6. An organosilane compound according to claim 1, wherein $R^2$ and $R^3$ are both a phenyl group.

7. An organosilane compound according to claim 1, wherein one of $R^2$ and $R^3$ is a phenyl group and the other is a methyl group.

8. An organosilane according to claim 1, wherein $R^1$ is a hydrogen atom.

9. An organosilane compound according to claim 1, wherein $R^1$ is a methyl group.

10. An organosilane compound of the following formula

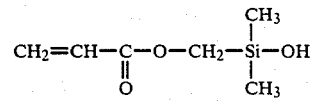

11. An organosilane compound of the following formula

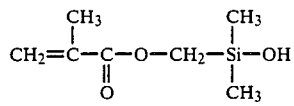
12. An organosilane compound of the following formula
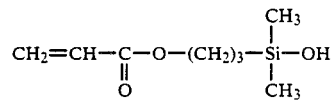
13. An organosilane compound of the following formula
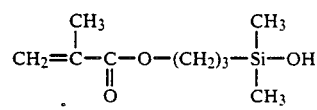
* * * * *